United States Patent [19]
Johnson

[11] Patent Number: 6,020,052
[45] Date of Patent: Feb. 1, 2000

[54] LAMINATED MEMBRANE STRUCTURE FOR POLAROGRAPHIC MEASUREMENT AND METHODS OF MAKING SAID STRUCTURES

[75] Inventor: Jay M. Johnson, Dayton, Ohio

[73] Assignee: YSI Incorporated, Yellow Springs, Ohio

[21] Appl. No.: 09/011,251

[22] PCT Filed: Jul. 30, 1996

[86] PCT No.: PCT/US96/12412

§ 371 Date: Jan. 28, 1998

§ 102(e) Date: Jan. 28, 1998

[87] PCT Pub. No.: WO97/04954

PCT Pub. Date: Feb. 13, 1997

[51] Int. Cl.[7] .............................. B32B 3/26; G01N 27/26
[52] U.S. Cl. .................................... 428/304.4; 428/318.4; 204/403; 204/415; 435/4; 435/817
[58] Field of Search .......................................... 428/304.4

[56] References Cited

U.S. PATENT DOCUMENTS

| | | | |
|---|---|---|---|
| 3,979,274 | 9/1976 | Newman | 204/195 B |
| 4,073,713 | 2/1978 | Newman | 204/195 B |
| 4,241,178 | 12/1980 | Esders et al. | 435/15 |
| 4,388,166 | 6/1983 | Suzuki et al. | 204/403 |
| 4,415,666 | 11/1983 | D'Orazio et al. | 435/179 |
| 4,418,148 | 11/1983 | Oberhardt | 435/179 |
| 4,467,811 | 8/1984 | Clark, Jr. | 128/635 |
| 4,484,987 | 11/1984 | Gough | 204/1 T |
| 4,759,828 | 7/1988 | Young et al. | 204/1 T |
| 4,786,597 | 11/1988 | Matson et al. | 435/41 |
| 4,795,707 | 1/1989 | Niiyama et al. | 435/288 |
| 4,832,797 | 5/1989 | Vadgama et al. | 204/1 T |
| 4,855,353 | 8/1989 | Kurami et al. | 525/54.1 |
| 4,886,740 | 12/1989 | Vadgama | 435/4 |
| 4,950,379 | 8/1990 | Young et al. | 204/403 |
| 5,196,340 | 3/1993 | Miyamoto | 435/288 |
| 5,352,348 | 10/1994 | Young et al. | 204/153.12 |
| 5,429,726 | 7/1995 | Johnson et al. | 204/153.12 |
| 5,437,973 | 8/1995 | Vadgama et al. | 435/4 |
| 5,520,788 | 5/1996 | Johnson | 204/415 |

FOREIGN PATENT DOCUMENTS

| | | |
|---|---|---|
| 1307826 | 9/1992 | Canada . |
| 0216577 | 4/1987 | European Pat. Off. . |
| 216111 | 11/1984 | Germany . |
| 54-43796 | 4/1979 | Japan . |
| 55-162051 | 12/1980 | Japan . |
| 59-164953 | 9/1984 | Japan . |
| 6232352 | 8/1985 | Japan . |
| 60-185153 | 9/1985 | Japan . |
| 61-145447 | 3/1986 | Japan . |
| 62-67442 | 3/1987 | Japan . |
| 1442303 | 7/1976 | United Kingdom . |
| 9204438 | 3/1992 | WIPO . |

OTHER PUBLICATIONS

Article: "The Effect Of Crosslink Density On Permeability In Biosensors: An Unsteady–State Approach" Biotechnology Techniques, vol. 9 No. 4, (1995) pp. 277–282 by Mehmet Mutlu and Selma Mutlu.

(List continued on next page.)

*Primary Examiner*—Ellen M. McAvoy
*Attorney, Agent, or Firm*—Biebel & French

[57] ABSTRACT

An improved laminated enzyme containing membrane for polarographic sensors and methods of making these membranes are disclosed. The laminated membrane comprises an outer, support layer having pores therein of greater than about 300 angstrom units in diameter and this outer membrane has a pore density of less than $6\times10^8$ pores/cm$^2$. The porosity of the outer membrane may be on the order of 0.001–0.2%. An enzyme layer is interposed between the support layer and an inner, barrier layer; the latter positioned near the working electrode of the polarographic cell. The enzyme layer comprises a buffer solution dispersed therein wherein the molarity of the buffer solution is between about $1\times10^{-6}$ to 0.1 M. The enzyme layer is highly dense as measured by a molar response ratio of ferrocyanide:$H_2O_2$ of less than about 0.05.

12 Claims, 12 Drawing Sheets

OTHER PUBLICATIONS

Article: "Generalized model for enzyme amperometric biosensors" Analytica Chimica ACTA 307 (1995), pp. 27–36 by Alexander Neikov and Sokol Sokolov.

Article: "A Model for the Amperometric Enzyme Electrode Obtained through Digital Simulation and Applied to the Immobilized Glucose Oxidase System" 1974 by Leroy D. Mell and J.T. Maloy.

Article: "The Size of Pores In Collodion Membranes" by David I. Hitchcock, Laboratories of The Rockefeller Institute for Medical Research, accepted for publication Mar. 1, 1926.

Article: "Statistical Evaluation Of Sieve Constants In Ultrafiltration" Laboratories of the Hopkins Marine Station, Pacific Grove, accepted for publication Nov. 30 1935 by John D. Perry.

Article: "Passage of Molecules Through Capillary Walls" by John R. Pappenheimer, Department of Physiology, Harvard Medical School p. 387–423, Jul. 1953.

Article: "Characterization of Biological Membranes by Equivalent Pores" by A.K. Solomon, Biophysical Laboratory, Harvard Medical School, Boston, MA. p. 335–364. Data N/A.

Article: "Filtration, Diffusion and Molecular Sieving Through Peripheral Capillary Membranes—A Contribution to the Pore Theory of Capillary Permeability" by J.R. Pappenheimer, E.M. Renkin and L.M. Borrero, Department of Physiology, Harvard Medical School, Boston MA, p. 13–46 Oct. 1951.

Hawley's Condensed Chemical Dictionary, Twelfth Edition, Revised by Richard J. Lewis, Sr (1981) Van Nostrand Reinhold Company, NY, pp. 11, 192, 237, 337, 492, 829.

Review: Transport Phenomena In Membranes, N. Lakshminarayanaiah, Academic Press, New York, 1969, submitted by Herbert P. Silverman, Ph.D.

Nuclepore Filtration Products for the Laboratory, Catalog LAB 30, p. 1–15., (date N/A).

"Hydrolysis of Cellulose Acetate and Cellulose Acetate Butyrate Pseudolatexes Prepared by a Solvent Evaporation–Microfluidization Method" Drug Development and Industrial Pharmacy, 19(5), 521–530 (1993) by Roland Bodmeier et al.

Article: "Elimination of the Acetaminophen Interference in an Implantable Glucose Sensor", Analytical Chemisty, vol. 66, No. 7, pp. 1183–1188 (1994) by Yanan Zhang et al.

Article: "Cellulose Acetate Ultrafiltration Membranes" Journal of Applied Polymer Science, vol. 19, pp. 1449–1460 (1975) by O. Kutowy et al.

Article: "Effect of Secondary Additives in Casting Solution on the Performance of Porous Cellulose Acetate Osmosis Membranes" Journal of Applied Polymer Science, vol. 17, pp. 2485–2499 (1973) by H. Kirk Johnston et al.

Article: "Effect of Casting Conditions on the Performance of Porous Cellulose Acetate Membranes in Reverse Osmosis" Journal of Applied Polymer Science, vol. 14, pp. 723–733 (1970) by B. Kunst et al.

"Paracetamol Interference with Glucose Analysis" The Lancet, Sep. 19, 1981.

"Paracetomol Interference with Glucose Analyser" Clinical Chemisty, vol. 27, No. 11 (1981).

"Electrochemical Interferences with the YSI Glucose Analyzer" Clinical Chemistry, vol. 28, p. 726 (1982).

"Paracetamol and Blood–Glucose Analysis with the YSI Analyzer" Clinical Chemistry, vol. 29, No. 12 (1983).

"Acetaminophen Overdose—A new–and treacherous–care problem" Registered Nurse Magazine, Dec. 1978 pp. 56–62 by John S. Jozwiak, R.N., B.S.N.

"Paracetamol Interference with YSI Glucose Analyzer" Clinical Chemistry, vol. 27, No. 5, pp. 782–783 (1981).

"Apparent hyperglycaemia in paracetamol overdose" British Journal of General Practice, Jun. 1992.

"Evaluation of the YSI 2300 Glucose Analyzer: Algorithm–corrected Results are Accurate and Specific", Clinical Biochemistry, vol. 29 (1996) by J. Rex Astles et al.

"Reverse Osmosis Membranes" Journal of Applied Polymer Science, 15, 1317, 1319 (date N/A).

"Internal membranes and laminates for adaptation of amperometric enzyme electrodes to direct biofluid analysis" Scan J. Clin Lab Invest 1993; 53, Suppl 214: 53–60 by Mohamed A. Desai et al.

"Amperometric enzyme electrodes for lactate and glucose determinations in highly diluted and undiluted media" Analytica Chimica Acta, 281 (1993) 489–502 by Dorothea Pfeiffer et al.

"Plasticized poly(vinyl chloride) as a permselective barrier membrane for high–selectivity amperometric sensors and biosensors" Analytica Chimica Acta, 269 (1992) 65–73 by I.M. Christie et al.

Journal of Applied Polymer Science, p. 1878 by R.E. Kesting et al. (date N/A).

Teijin, "UltraFiltration Membranes", CA 99:106450 (1983).

Teijin, "Cellulose Membranes", CA 99:72428 (1983).

Teijin, "Semipermeable Membranes", CA 98:5241 (1981).

He, "CA–CAB Mixed Membranes", CA 116:241635 (1991).

Article: Advances in Biosensors, Yacynych, (1992), vol. 2 (A.P.F. Turner ed.) pp. 24–25 JAI Press Ltd.

Article: "Effect of Enzyme–matrix Composition on Potentiometric Response to Glucose Using Glucose Oxidase Immobilized on Platinum", Wingard L.B. and Canton L.A., Castner J.F., Biochemica et Biophysics Acta, vol. 748, 1983 pp. 21–27.

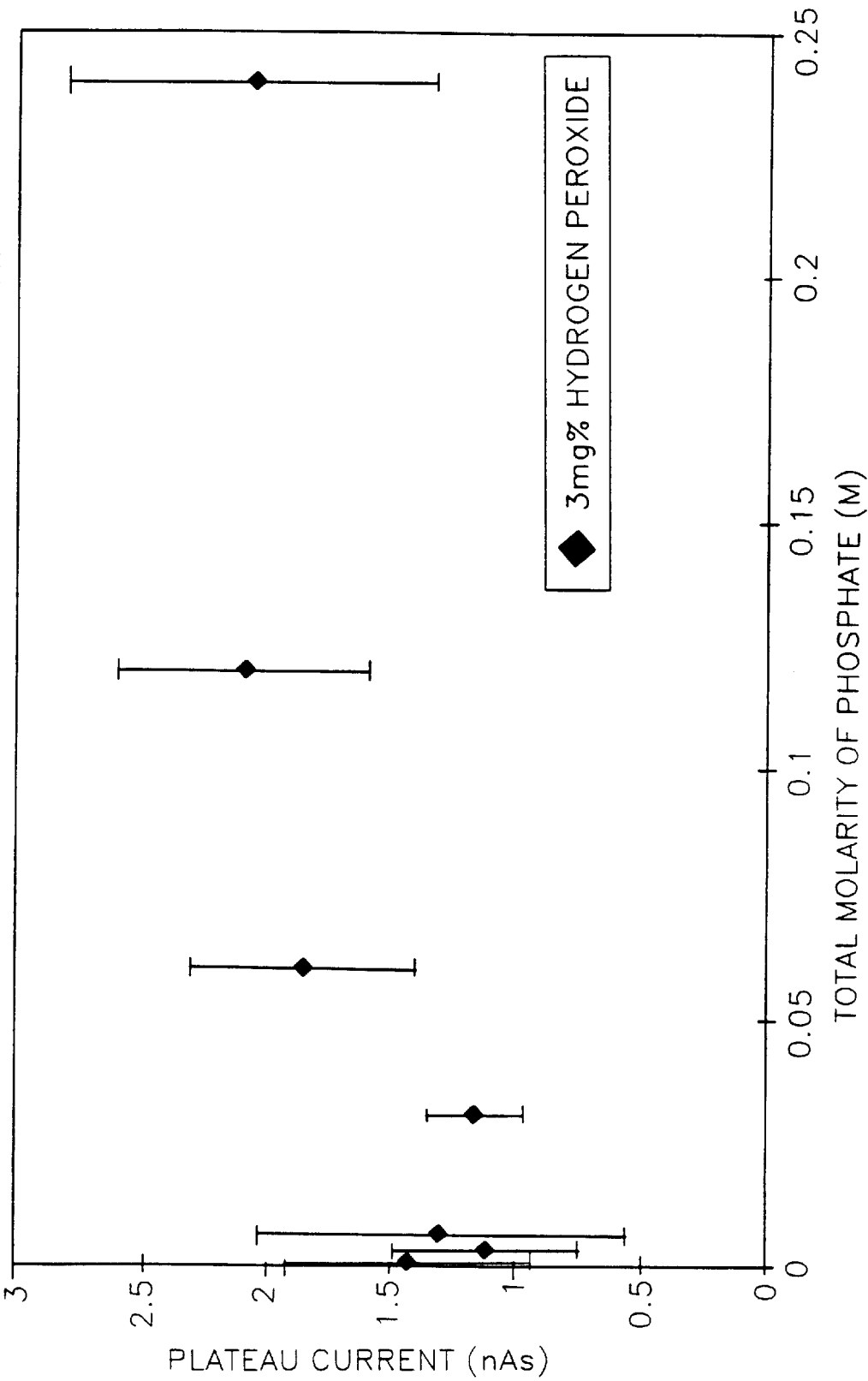

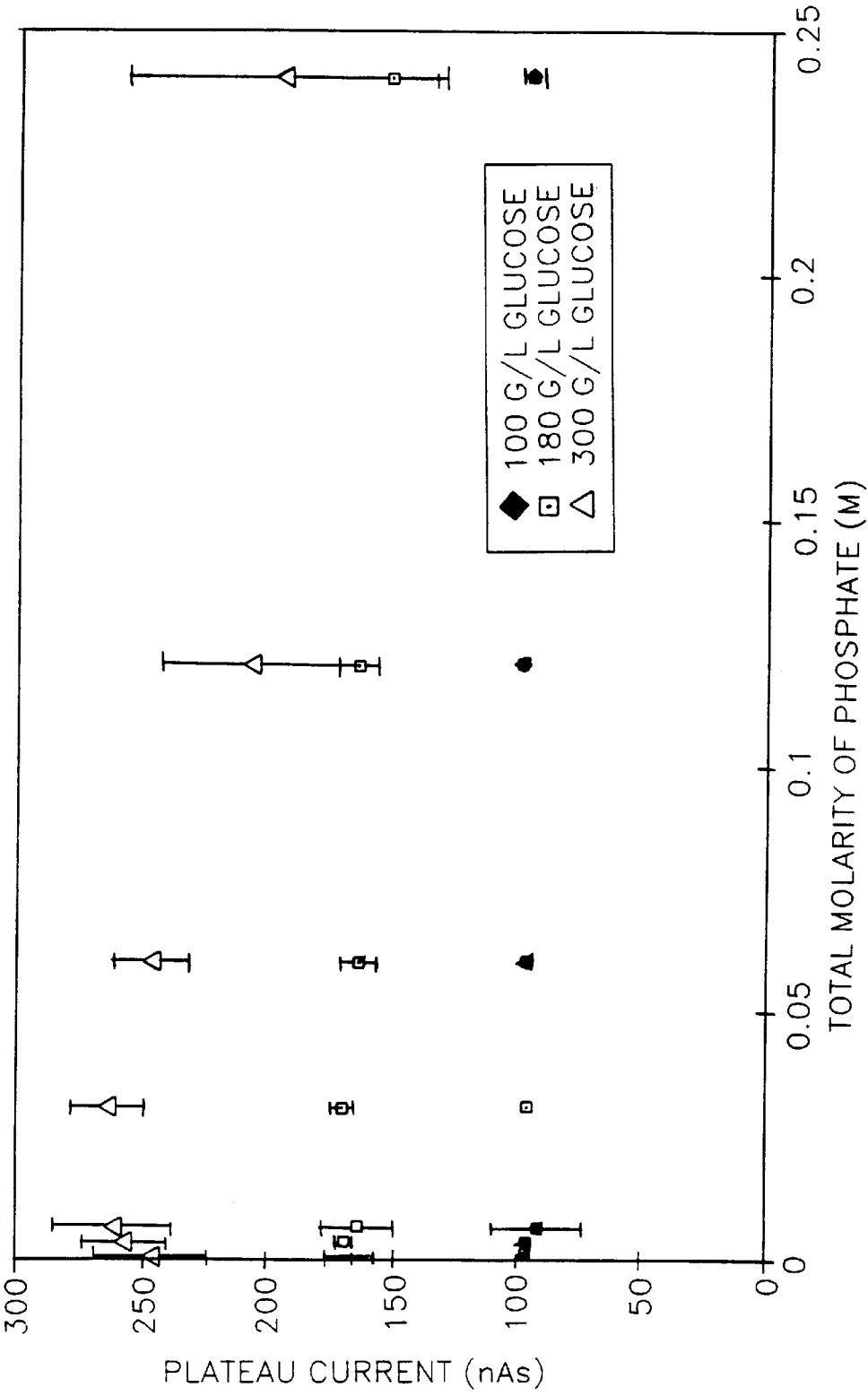

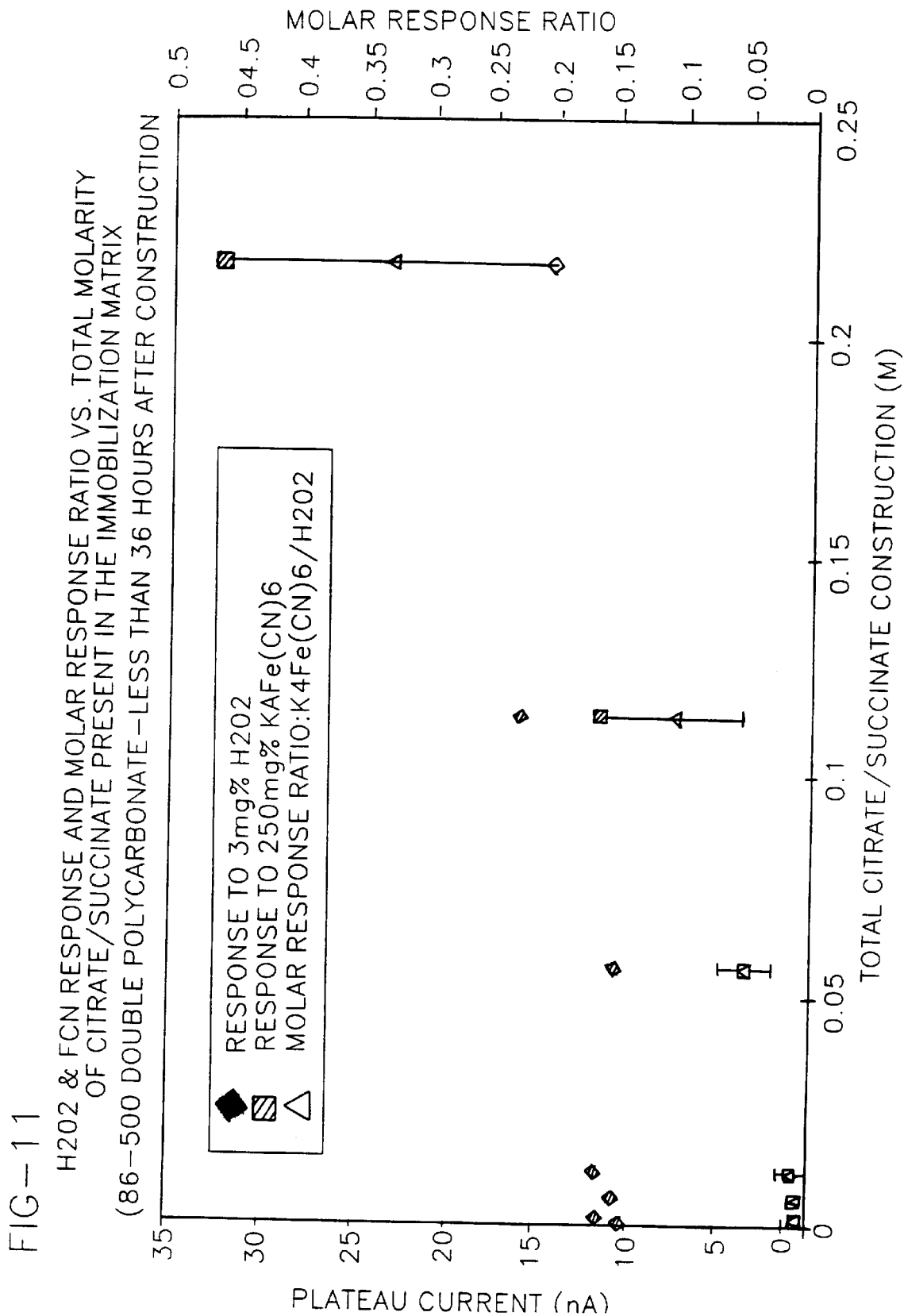
FIG-11 H2O2 & FCN RESPONSE AND MOLAR RESPONSE RATIO VS. TOTAL MOLARITY OF CITRATE/SUCCINATE PRESENT IN THE IMMOBILIZATION MATRIX (86-500 DOUBLE POLYCARBONATE-LESS THAN 36 HOURS AFTER CONSTRUCTION)

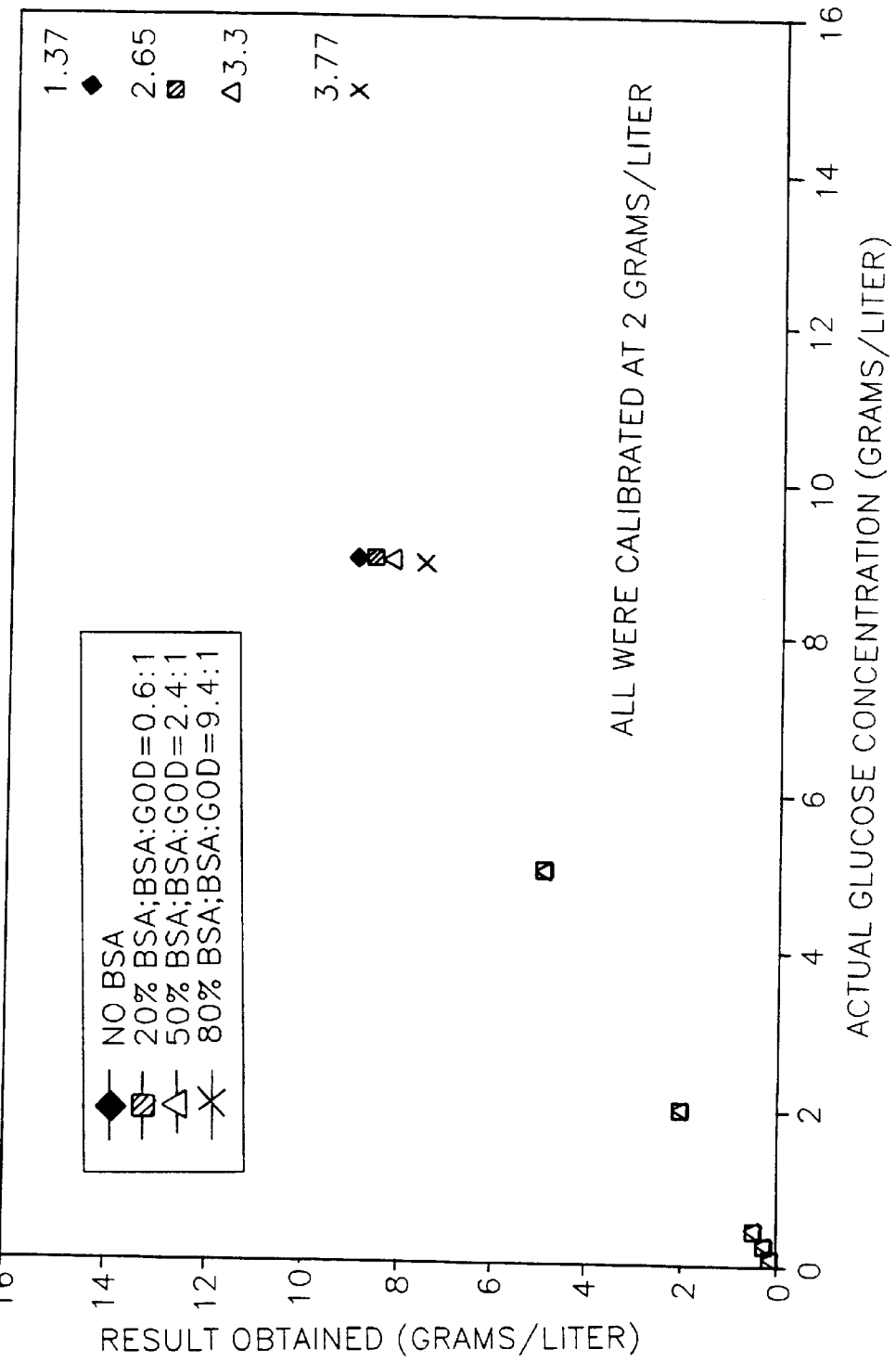

LAMINATED MEMBRANE STRUCTURE FOR POLAROGRAPHIC MEASUREMENT AND METHODS OF MAKING SAID STRUCTURES

FIELD OF THE INVENTION

The present invention pertains to an improved laminated membrane structure adapted for use in conjunction with an enzyme electrode and to methods for making this laminated structure.

BACKGROUND OF THE INVENTION

Polarographic cell systems have met with wide acclaim particularly in the medical field, providing for detection and concentration measurement of many desired analytes. Enzymes are commonly used in such systems, especially in those situations wherein the analyte itself is not polarographically active but where a reaction product formed or reactant consumed by an enzymatic reaction with the analyte is polarographically active.

For example, in medical applications, one common procedure is to measure glucose in the blood of a patient. Typically, blood samples are withdrawn from the patient for an analysis for glucose concentration using a glucose oxidase electrode with a polarographic detector for detecting $H_2O_2$ generated in accordance with the reaction:

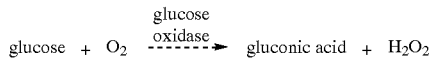

$$\text{glucose} + O_2 \xrightarrow{\text{glucose oxidase}} \text{gluconic acid} + H_2O_2$$

The hydrogen peroxide generated by the reaction is measurable by a polarographic detector and, by appropriate calibration and calculation, glucose content in the sample can be accurately determined by the $H_2O_2$ formed in the reaction.

The polarographic cell systems commonly used for these measurements include an enzyme containing laminated membrane that separates the analyte sample from the working electrode of the cell. These types of membranes are disclosed in the U.S. Pat. Nos. 3,979,274 and 4,073,713 (Newman), both patents being hereby incorporated by reference herein. In such membranes, a thin innermost membrane referred to as a barrier layer composed of cellulose acetate, silicone rubber, or methyl methacrylate is located adjacent the working electrode of the polarographic cell. Glucose oxidase enzyme is interposed between this barrier layer and an outer polycarbonate support layer. The outer support layer is typically about 5 um in thickness and is in contact with the analyte containing sample.

In a glucose analytical determination, glucose and oxygen permeate through the outer support layer and react in the presence of the enzyme. Hydrogen peroxide produced permeates through the inner barrier layer where it is polarographically detected. The support layer permits passage of glucose, oxygen and other molecules therethrough while not permitting passage of high molecular weight substances such as proteins, red blood cells and other macromolecules.

The barrier layer permits access of hydrogen peroxide to the working electrode while blocking passage of substances having molecular weights on the order of about 150 and greater such as ascorbic acid and uric acid.

It has been ascertained that in order to provide accurate linear measurement in solutions containing high glucose concentrations, such as in whole blood, plasma or serum, it is desirable to inhibit diffusion of the glucose to the enzyme layer relative to oxygen migration thereto. Otherwise, the ratio of glucose to oxygen contacting the enzyme is unfavorable and makes the oxygen content, rather than the glucose concentration of the sample, the rate limiting component of the reaction. In turn, this leads to inaccurate glucose concentration measurements by the instrument. Linearity, in such situations, occurs only over a range of low glucose concentration. This problem is not only limited to glucose determination but is also experienced in the measurement of other analytes, such as lactate.

In order to overcome this problem, it has been common practice to dilute the glucose and lactate concentrations of the sample so that the as measured analyte concentration level is within the range of concentration exhibiting linearity. However, it is often time consuming and impractical to dilute the analyte containing sample. Additionally, it is becoming commonplace to measure for analytes such as glucose or lactate on a single analytical testing device which incorporates other measurement channels as well. These other channels require undiluted whole blood or plasma as the analyte sample input; therefore requiring that the glucose and/or lactate measurement channel also function to measure analyte in the same undiluted whole blood or plasma sample medium.

In order to provide accurate glucose or lactate measurement in whole blood, the sample contacting membrane layer of the Newman type membranes has been modified to limit diffusion of the analyte to the enzyme layer. For example Japanese patent application Sho 59-40182 disclosed that the pore size of the outer sample contacting membrane should be 200 Å or less, with tested 150 Å pore sizes showing improved glucose measurement in whole blood samples. Later, in an obvious variation from the teachings of the Japanese reference, Young et al. in U.S. Pat. No. 4,759,828 indicated that the outer sample contacting layer should have pore sizes on the order of about 10–125 Angstrom units in diameter. The '828 patent expressly indicates that outer layers of 150 Angstrom unit pore size will not "sufficiently limit the diffusion of glucose molecules to allow glucose measurements to be made on undiluted serum."

In addition to the emphasis placed on small pore sizes in the outer, solution contacting layers of the laminated membrane, Vadgama et al. have emphasized the importance of low porosity materials. Percentage porosity is defined as the product of pore density×pore area×100. Porosities in the range of 0.001% or 0.005% to 0.5% and in general less than 2% are taught in Vadgama et al. E.P. Application 0 216 577. See also U.S. Pat. No. 5,437,973 (Vagdama et al.).

The move towards use of small pore size support layers has not been without problem. For example, during the fabrication of small pore size films of the type used as outer, solution contacting, layers in laminated enzyme containing membranes, the pores are often formed by an irradiation process in which fission fragments from an uranium atom or other forms of irradiation pierce the solid film precursor to form the desired film pore density. Pore sizes are established in a subsequent etching step using a strong alkali solution. In the final stages of this process, films are washed or treated with high molecular weight surfactants such as polyvinylpyrrolidone.

Poor uniformity has beet experienced when these films are incorporated into laminated enzyme containing membranes. It is thought that the large, bulky surfactant molecules used during the film fabrication processes tend to block or clog some of the pores. Because this can occur to different degrees within the relatively small unit area of the film which ultimately is used in a enzyme containing laminated membrane, relatively large membrane to membrane inconsistencies may be experienced. Small pore sizes, in general, also make it difficult to attain membrane uniformity during membrane manufacture.

Additionally, when small pore sized support membranes are used, the potential for clogging or obstruction during use in the analytical process is also present.

Accordingly, there is a need in the art for the provision of an enzyme containing laminated membrane assembly that is capable of measuring glucose and/or lactate in undiluted whole blood, plasma or serum which will not suffer from the aforementioned problems.

SUMMARY OF THE INVENTION

These and other objects are met by the laminated membranes herein disclosed and claimed. Basically, the invention provides improvement over the membranes disclosed in the aforementioned Newman patents. One aspect of the invention resides in the construction of the outer layer or, as it is sometimes referred to, the support layer of the laminated membrane.

Contrary to the teachings in the prior art, it has been discovered that the outer layer of the laminated membrane should be provided with super large pore sizes. These large pores are difficult to block or clog when the film is washed or treated with large surfactant molecules or during use in an analytical instrument. At the same time, these outer layers function to inhibit glucose or lactate diffusion to the enzyme layer so as to allow for measurement to be made in undiluted whole blood or plasma samples.

The outer semi-permeable membrane has pore sizes of greater than about 300 angstrom units (e.g. greater than 270 angstrom units) in diameter and has a pore density of less than $6 \times 10^8$ pores/cm$^2$. Preferably, the porosity of the outer semi-permeable membrane is within the range of 0.001–0.2%.

In another aspect of the invention, it has been found that a highly dense enzyme layer itself also leads to improved dynamic range or linearity. For example, it has been found that the concentration of the buffer, in the buffer solution mixed with enzyme during the immobilization procedure, should be controlled to within the range of about $1 \times 10^{-6}$–0.1 M, preferably within the range of $1 \times 10^{-6}$–0.05 M and most preferably within the range of 0.001–0.005 M. Surprisingly, it has been found that as the buffer concentration decreases, linearity of the response of sensors employing these improved membranes is improved.

The invention will be further described in conjunction with the following detailed description read in view of the drawings.

BRIEF DESCRIPTION OF THE DRAWINGS

FIG. 9 is a graph similar to FIG. 6 but showing data obtained using the second buffer solution and third laminated membrane construction;

FIG. 10 is a graph similar to FIG. 7 but showing data obtained using the second buffer solution and third laminated membrane construction;

FIG. 11 is a graph plotting currents obtained on the YSI Model 2700 analyzer for varying amounts of ferrocyanide and $H_2O_2$ samples tested using a specially constructed laminated enzyme containing membrane to demonstrate the importance of providing a highly dense enzyme layer; and FIG. 12 is a graph showing actual results obtained vs. expected results using the Model 2700 with no buffer salt present in the enzyme layer during its preparation but with increasing amounts of bovine serum albumin (BSA) therein.

DETAILED DESCRIPTION

Figure 1:
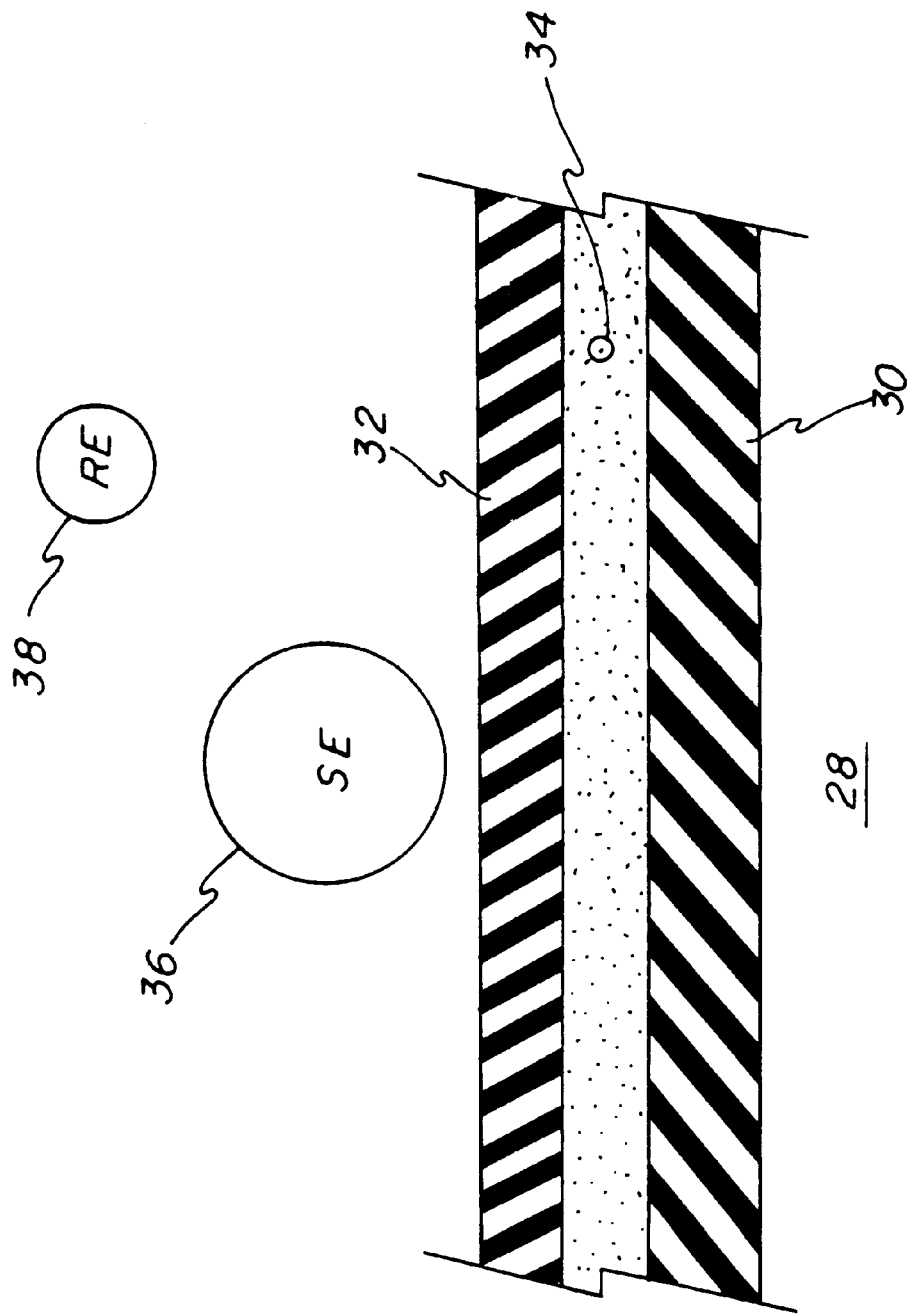
FIG. 1 is an enlarged schematic view of a cross section of an enzyme containing laminated membrane in accordance with the invention.

With reference to FIG. 1, there is shown an enlarged cross-section of an enzyme containing laminated membrane 28. Membrane 28 is adapted for use in conjunction with commercially available analytical equipment capable of measuring, for example, glucose or lactate concentration, in undiluted whole blood, plasma or serum solutions.

Barrier layer 32 comprises an homogenous cellulose acetate/cellulose acetate butyrate polymer blend having a thickness of 2 microns or less, preferably 1–2 microns. Enzyme 34 is provided intermediate barrier layer 32 and support layer 30. Enzyme 34 is typically cross-linked in situ between the layers 32, 30 by use of glutaraldehyde although any one of a number of adhesives or cross-linking promoters may be used. Also, it should be mentioned that the enzyme itself may be used as the adhesive without any additional adhesive or cross-linking agent added.

Outer layer or support layer 30, may be comprised of a polycarbonate polymer. It is noted however, that the polymeric identity is not critical. For example, the layer 30 may also comprise polyurethane, regenerated cellulose or other polymer construction. Typically layer 30 will have a thickness of about 5 to 10 microns.

As shown, support layer 30 comprises a single layer. It is to be understood however, that the support layer 30 may actually comprise a multi-layered structure with, for example, bovine serum albumin or other suitable adhesive interposed between layers to yield a composite structure. In this approach pore sizes and individual thicknesses of the layers can be controlled, for instance, to limit or promote migration of a given chemical species to the enzyme 34.

It is to be appreciated that support layer 30 is positioned adjacent the analyte sample and that the barrier layer 32 is therefore adjacent a sensor electrode 36 (typically platinum) in an electrolyte solution. A reference electrode 38 is also disposed in the electrolyte. Accordingly, a polarographic cell is provided in which the electrodes and electrolyte are separated from the analyte solution by the laminated membrane.

As used throughout this disclosure, enzyme 34 will be described as glucose oxidase enzyme. The artisan of course will appreciate that depending on the particular desired analyte and reaction chosen, the enzyme may vary. For instance in analytical situations in which it is desired to monitor lactate levels in blood samples, lactate oxidase will be used as enzyme 34. Other candidate analytes and corresponding oxidoreductase enzymes are noted as being exemplary:

| analyte | oxidoreductase enzyme |
|---------|----------------------|
| lactose | galactose oxidase |
| sucrose | ( invertase<br>( mutarotase<br>( glucose oxidase |
| alcohol | alcohol oxidase |
| galactose | galactose oxidase |

Membrane 32 is preferably composed of a blend of cellulose acetate/cellulose acetate butyrate cellulosic esters. The ratio (by weight) of cellulose acetate: cellulose acetate butyrate used to form barrier layer 32 varies widely over a range of 1.5–20:1. Based upon present indications, it is preferred to utilize a 4:1 (by weight) blend of cellulose acetate/cellulose acetate butyrate to cast the film used to form barrier layer 32 of membrane 28.

The requisite ratio of cellulose acetate and cellulose acetate butyrate is dissolved in a two solvent system. The first solvent is a highly volatile organic solvent exhibiting a low boiling point. At present, nitromethane, dimethylformamide and cylcohexanone may be mentioned as being exemplary members of this class of highly volatile organic solvents. All of those have boiling points, under atmospheric conditions, of less than 200° C. At present, it is preferred to use nitromethane as the highly volatile organic solvent.

In addition to use of the volatile solvent, an organic liquid plasticizer is used as a second component of the casting solution. The CA/CAB blend is also soluble in the plasticizer. This plasticizer is characterized by having a boiling point of greater than about 200° C. and must be capable of rendering the CA and CAB compatible (i.e. leading to the formation of a homogenous CA/CAB film). Exemplary organic liquid plasticizers include the phthalates, phosphates, lactones and esters of aliphatic dibasic acids, camphor, etc. Especially preferred are the lactones including γ-butyrolactone and valerolactone. γ-Butyrolactone is presently preferred.

One of the surprising properties of butyrolactone and valerolactone is that they have high boiling points for such tiny molecules.

It is thought that the highly volatile solvent leaves the casting solution quickly while the plasticizer leaves the solution much more slowly and ultimately defines the pores in the layer as it leaves. It is preferred that the plasticizer have a boiling point of about 80° F. higher than the volatile organic solvent. Since the highly volatile organic solvent will leave the solution first, the viscosity of the film increases rapidly enough so that it does not flow or sag appreciably after it is cast. The plasticizer helps to ensure that the cast film maintains its structural integrity with the pores in the film then being defined as it, the plasticizer solvent evaporates.

The first and second solvents can be used in a wide range of addition to the cellulosic esters. The volume ratio of Volatile Organic Solvent:Plasticizer may for instance vary from about 0.5–1.5 solvent:plasticizer with a ratio of about 1:1 presently preferred.

The volatile organic solvent and plasticizer must be essentially free of high molecular weight impurities, because such impurities would become concentrated as the film dries and would exert an influence on the film out of proportion to their percentage in the starting solvent.

The shape of the plasticizer molecule may also have an influence on pore geometry of the barrier layer. Current wisdom is to the effect that linear molecules move through a film by "reptating" (i.e. a snake-like motion) which can allow the plasticizer to escape through a very irregular and tortuous pore. A substantially spherical molecule such as γ-butyrolactone, on the other hand, has a definite diameter and results in a pore at least equal to that diameter to escape. This suggests that more spherical plasticizer molecules will produce a better-defined pore as they depart from the film.

In addition to the solvent and plasticizer, described supra., a thinner or diluent may be added, as necessary, to accurately control the viscosity of the casting solution. For example, isopropanol, methyl ethyl ketone and ethyl acetate may be mentioned as exemplary. The thinner may be added in an amount by weight of about 0.5–1.5:1 based on the weight of plasticizer added. Presently, it is preferred to use isopropanol as the thinner, present in amount of 0.88 parts by weight isopropanol: parts by weight plasticizer.

The cellulose esters are added to the highly volatile organic solvent and plasticizer in an amount sufficient to make 10–40 wt. % solutions of (cellulose esters): combined weight of cellulose esters+solvent and plasticizer).

The cellulose acetate butyrate (CAB) that is used comprises a mixture of cellulose acetic acid esters and butyric acid esters. Commercially available CABs are graded according to butyryl content of 17, 27, 38, and a 50%. Presently preferred is a CAB product having 28–31% acetyl groups and about 16% butyryl. This product is available from Eastman Kodak.

Turning back now to the construction of the support layer in accordance with the invention, support layer 30 is preferably provided with large pores on the order of at least about 300 A units in diameter. Layer 30 has a pore density of less than $6 \times 10^8$ pores/cm$^2$ and exhibits a porosity of (pore area×pore density×100) of between about 0.001 to 0.200%. Semi-permeable films having these properties are available from Poretics, Inc. of Livermore, Calif.

Most preferably, layer 30 comprises pores on the order of about 310 to about 750 angstrom units in diameter and a percentage porosity of from about $1 \times 10^{-1}$ to $5 \times 10^{-3}$. Especially preferred is a polycarbonate layer having a pore size of about 310 angstrom units with a pore density of $1 \times 10^8$ pores/cm$^2$ and a resulting percentage porosity of $7.53 \times 10^{-2}$.

Examples of other exemplary semi-permeable films useful as layer 30 include the following:

| Pore Size Diameter - Angstrom Units | Pore Density | Percentage Porosity |
| --- | --- | --- |
| 686 | $6 \times 10^6$ | $2.21 \times 10^{-2}$ |
| 450 | $6 \times 10^6$ | $9.53 \times 10^{-3}$ |
| 382 | $3 \times 10^7$ | $3.6 \times 10^{-2}$ |
| 343 | $1 \times 10^8$ | $9.23 \times 10^{-2}$ |

As explained previously, enzyme 34 is usually immobilized intermediate barrier layer 32 and support layer 30 by the use of glutaraldehyde or similar adhesive and/or cross linking agent. A solution of about 1–15 wt % of glutaraldehyde containing solution is admixed with the enzyme 34. Typically, a buffer solution is admixed with the glutaraldehyde—enzyme in order to maintain a favorable pH environment of about 4–9 so that the reaction proceeding in the enzyme layer proceeds under relatively constant, favorable conditions. Overall, the thickness of this layer or enzyme containing matrix is about 0.1–0.2 um.

When making the laminated membranes, the enzyme containing mixture including buffer is interposed between the support layer and barrier layer. A slight compressive force may be applied so as to provide a sandwich type structure. The laminated structure is then allowed to dry via ambient conditions and/or in an oven. Preferred conditions call for air drying for about one-half hour followed by oven drying at about 45° C. for about 30 minutes.

O-rings or the like may then be glued to the outer surface of the laminated membrane to facilitate use of the membrane in the desired analytical instrument, such as a YSI Model 2700 analyzer. These membranes are preferably refrigerated prior to usage.

Quite surprisingly, it has been found that reduced amounts of buffer in the buffer solution admixed with the enzyme actually increase the linearity of response of the sensor. Although Applicant is not to be bound to any particular theory of operation, it is thought that diminished amounts of buffer in the immobilized enzyme matrix actually serve to increase the density of the enzyme containing matrix therefore impeding the flux of glucose or other analyte to and through the enzyme layer.

The buffer is present in the immobilization solution in an amount of between about 0.001–0.1 molar. Preferably, it is present in an amount of about 0.001–0.050. More preferable is a buffer concentration range of between about 0.001–0.005. Based upon presently available data, buffer concentration should most preferably be about 0.001 M.

In commercial prior art practice, it was common to use buffer salt concentrations in the enzyme immobilization matrix of about 0.029–0.043 molar. However, enzyme layers so prepared were used in conjunction with diluted glucose sample analyses wherein the outer polycarbonate support layer of the laminated assembly typically had pore sizes on the order of about 300 angstroms with a pore density of $6 \times 10^8$ pores/cm². It was not to be expected from this prior commercial practice, that decreasing buffer concentration to, in effect, increase the density of the enzyme layer would lead to increased linearity for making undiluted blood or plasma measurements; especially in conjunction with the concurrent use of support layer pore sizes of about 300 angstroms and greater and pore densities of less than $6 \times 10^8$ pores per cm².

As to the particular buffer solutions that may be used, these are not critical. The buffer should however be capable of maintaining the pH of the enzyme containing layer within the range of about 4–9. Exemplary buffer compositions are those known in the art and include

- acetic acid-sodium acetate
- ammonium hydroxide-ammonium chloride
- phosphate based buffers
- carbonate based buffers
- citrate based buffers
- succinate based buffers
- glycine based buffers
- maleate based buffers and generally the list of biochemical buffers listed on pages 79–82 of Concise Encyclopedia Biochemistry, Second Edition, Walter de Gruyter, 1988.

The buffer used in the Example 1 and 2 studies reported hereinbelow is a trisodium citrate/succinic acid buffer wherein the citrate compound is present in a ratio (by weight) of about 8:1 based on the weight of the succinic acid. These compounds are mixed with about 0.25 parts, by weight, based upon the succinic acid, of a potassium salt of EDTA. This particular buffer has a useful pH range of no greater than 4.0 to 6.0.

The invention will now be further described with respect to the following examples, which are not to be construed as being constrictive in any manner. The examples are set forth below only to illustrate the operative principles of the invention.

EXAMPLE ONE

In order to evaluate the effects of changing the concentration of the buffer (pH 5.4–5.6 Na citrate/succinic acid) used in the enzyme immobilization matrix of a Newman style, laminated, glucose oxidase containing membrane, the following procedures were performed.

1. Materials

Glucose oxidase membranes were constructed using a cellulose acetate/cellulose acetate butyrate membrane (1–2 um thick) manufactured by YSI as the inner layer and a 10 um thick outer polycarbonate membrane have an average pore diameter size of 310 angstroms in diameter and a pore density of $1 \times 10^8$ pores/cm².

2. Membrane Construction a) 10 mg of glucose oxidase (BMC catalogue #105 107) were dissolved in 100 uL of DI H$_2$O and stirred for 10 minutes to allow dissolution.

b) 150 uL of a 2.5% glutaraldehyde solution containing the citrate/succinate buffer mentioned above were added to the enzyme/H$_2$O solution and then the combined solution was stirred for 60 minutes at room temperature.

c) A small drop of the resulting solution (i.e. resulting from step (b)) was then applied to the surface of the cellulose acetate membrane.

d) A piece of the polycarbonate membrane was then immediately applied over the top of this solution and the solution was allowed to wick/spread between the two layers.

e) Light pressure was then applied to a large rubber stopper that was rolled across the surface of the laminate and an absorbent tissue was used to absorb excess solution.

f) The membrane was then air dried for 30 minutes at room temperature and was then oven dried at 45° for 30 minutes.

g) Silicone rubber O-rings were glued to the outer surface of the laminated membrane to facilitate membrane use in the analytical test instrument.

The above procedure was repeated a number of times changing only the concentration of the citrate/succinate buffer added to the 2.5% glutaraldehyde solution. All membranes were stored in the refrigerator until they were evaluated.

3. Membrane Evaluation Procedure

Membranes were evaluated in a YSI Model 2700 select—dual channel analyzer using a YSI 2357 phosphate buffer (pH 7.2) as the internal buffer. Eight membranes of each type were evaluated, one on each of eight different hydrogen peroxide electrodes. After the membranes were installed on the instrument and the reported background current had dropped below 6 nanoamps, calibration was achieved using a known 40 g/liter glucose solution. (Actual glucose concentration in the 2700 sample chamber was 2 g/liter or 200 mg % due to the fact that each sample is automatically diluted at 20:1 dilution ratio as it is injected into the sample channel of the 2700 instrument).

A number of glucose solutions covering a wide range of concentration were then run in triplicate. A 3 mg % hydrogen peroxide solution (no glucose) was also run as a sample. Plateau currents (at a 30 second read time) glucose readings and the slopes of the response curves were tabulated. (The slope of the response curve is a measure of speed of response and is measured by taking ten readings between 20 and 30 seconds after sample injection and calculating the average change in current per minute).

For each membrane type, the average plateau current, average slope and average glucose reading obtained for each solution were calculated.

4. Results

The data obtained as a result of the study are reported in Table One–Three following.

TABLE ONE

| Total Molarity Cit/Suc | 3 mg % H2 | 1.8 g/L | 5 g/L | 9 g/L | 40 g/L | 100 g/L | 180 g/L | 300 g/L |
|---|---|---|---|---|---|---|---|---|
| Average Readings Grams/Liter | | | | | | | | |
| 0 | 1.685833 | 1.584167 | 4.917917 | 9.022917 | 40 | 99.07083 | 174.2917 | 284.3333 |
| 0.0014 | 1.680833 | 1.62125 | 4.982917 | 9.052917 | 40 | 98.62917 | 172.75 | 278.9583 |
| 0.0057 | 1.655833 | 1.576667 | 4.9275 | 9.008333 | 40 | 98.525 | 173.375 | 278.75 |
| 0.057 | 1.425 | 1.61875 | 4.9575 | 9.05375 | 40 | 98.82083 | 174.0417 | 274.9167 |
| 0.114 | 1.17875 | 1.701667 | 5.028333 | 9.129167 | 40 | 97.27083 | 165.625 | 248.0833 |
| 0.2166 | 0.83275 | 1.746667 | 5.11375 | 9.267083 | 40 | 90.275 | 128.2833 | 163.1778 |
| Std Dev Readings (Grams/Liter) | | | | | | | | |
| 0 | 0.144351 | 0.11128 | 0.125204 | 0.182778 | 0 | 1.225708 | 2.13391 | 9.901098 |
| 0.0014 | 0.143878 | 0.131679 | 0.105811 | 0.107178 | 0 | 1.177492 | 4.018805 | 6.850878 |
| 0.0057 | 0.170068 | 0.133881 | 0.150889 | 0.135342 | 0 | 1.222507 | 2.663316 | 5.073273 |
| 0.057 | 0.14245 | 0.100884 | 0.117159 | 0.166051 | 0 | 1.942992 | 2.615203 | 10.02814 |
| 0.114 | 0.087286 | 0.060605 | 0.072001 | 0.108974 | 0 | 1.34677 | 4.34408 | 21.01228 |
| 0.2166 | 0.090006 | 0.079122 | 0.104356 | 0.15627 | 0 | 6.075628 | 26.52348 | 95.54377 |

TABLE TWO

| Total Molarity Cit/Suc | 3 mg % H2 | 1.8 g/L | 5 g/L | 9 g/L | 40 g/L | 100 g/L | 180 g/L | 300 g/L |
|---|---|---|---|---|---|---|---|---|
| Average Slopes (nAs/Min) | | | | | | | | |
| 0 | 0.135 | 0.264167 | 0.989583 | 0.1879167 | 8.208801 | 19.02375 | 39.62042 | 54.66583 |
| 0.0014 | 0.084583 | 0.248333 | 1.040417 | 2.052083 | 8.773377 | 22.49125 | 44.31125 | 50.94958 |
| 0.0057 | 0.149583 | 0.307917 | 1.17625 | 2.243333 | 9.859889 | 24.5575 | 48.78583 | 43.77125 |
| 0.057 | 0.205 | 0.425833 | 1.546667 | 2.94 | 12.70475 | 32.22625 | 59.39375 | 64.83667 |
| 0.114 | 0.2225 | 0.600833 | 2.139167 | 4.037917 | 17.44374 | 41.35958 | 56.26708 | 39.94542 |
| 0.2166 | 0.142917 | 1.001667 | 3.288333 | 5.7 | 19.81131 | 25.48625 | 32.7275 | 37.10833 |
| Std Dev Slopes (nAs/Min) | | | | | | | | |
| 0 | 0.129185 | 0.146469 | 0.388887 | 0.741829 | 3.246547 | 8.255991 | 16.57008 | 23.06155 |
| 0.0014 | 0.048072 | 0.081143 | 0.212487 | 0.505013 | 1.703857 | 5.992407 | 13.55391 | 31.8957 |
| 0.0057 | 0.109941 | 0.129455 | 0.44559 | 0.831766 | 3.74361 | 10.53729 | 18.1345 | 27.6139 |
| 0.057 | 0.134341 | 0.157205 | 0.4738983 | 0.870497 | 3.994135 | 13.22081 | 20.15855 | 24.1601 |
| 0.114 | 0.173001 | 0.299718 | 0.862668 | 1.570084 | 6.129219 | 15.37728 | 19.73034 | 30.88974 |
| 0.2166 | 0.245793 | 0.663961 | 1.857768 | 3.16269 | 11.49876 | 17.07517 | 20.6207 | 22.27205 |

TABLE THREE

| Total Molarity Cit/Suc | 3 mg % H2 | 1.8 g/L | 5 g/L | 9 g/L | 40 g/L | 100 g/L | 180 g/L | 300 g/L |
|---|---|---|---|---|---|---|---|---|
| Average Plateau (nAs) | | | | | | | | |
| 0 | | 1.085 | 1.060833 | 3.4 | 6.3375 | 27.90971 | 65.10333 | 123.8892 | 207.1996 |

TABLE THREE-continued

| Total Molarity Cit/Suc | 3 mg % H2 | 1.8 g/L | 5 g/L | 9 g/L | 40 g/L | 100 g/L | 180 g/L | 300 g/L |
|---|---|---|---|---|---|---|---|---|
| 0.0014 | 1.12125 | 1.1475 | 3.645 | 6.805417 | 29.91501 | 74.7225 | 133.6483 | 226.2767 |
| 0.0057 | 1.333333 | 1.359583 | 4.267917 | 7.892917 | 34.76109 | 85.88708 | 152.6725 | 250.9946 |
| 0.057 | 1.4375 | 1.694187 | 5.25375 | 9.72375 | 43.21686 | 107.4954 | 192.8158 | 313.6908 |
| 0.114 | 1.974583 | 2.955833 | 8.865 | 16.3 | 72.35563 | 176.5971 | 311.0025 | 475.2313 |
| 0.2166 | 3.00625 | 6.565417 | 19.53333 | 35.83917 | 154.4157 | 347.2736 | 441.5604 | 499.1572 |
| | | | Standard Deviation Plateau Currents (nAs) | | | | | |
| 0 | 0.248347 | 0.250530 | 0.732876 | 1.341777 | 6.15201 | 16.8299 | 25.86264 | 39.76761 |
| 0.0014 | 0.150922 | 0.101712 | 0.35099 | 0.667245 | 3.225406 | 7.164992 | 15.18709 | 33.588 |
| 0.0057 | 0.363266 | 0.480163 | 1.313192 | 2.28907 | 10.13812 | 24.35003 | 42.88546 | 72.8841 |
| 0.057 | 0.295311 | 0.348652 | 0.978928 | 1.767778 | 7.431495 | 17.67915 | 31.76288 | 46.67694 |
| 0.114 | 0.26919 | 0.47938 | 1.3992 | 2.591501 | 10.7905 | 26.83447 | 41.96145 | 37.94628 |
| 0.2166 | 1.072164 | 2.614743 | 7.713443 | 13.91256 | 58.87888 | 118.0389 | 97.6404 | 57.77174 |

A few significant trends can be observed in the data. First, the average plateau current obtained for any given glucose solution tends to increase as the concentration of the citrate/succinate buffer in the glucose immobilization matrix is increased. This is specifically shown in FIG. 2 for the response to the 40 g/l calibrator. FIG. 3 shows that exactly the same response trend is observed for the 3 mg % hydrogen peroxide solution as the citrate/succinate buffer is increased. Most importantly, the linear range of the membrane increases as the buffer concentration is decreased. This is illustrated in FIG. 4 which gives the average result obtained at high glucose concentrations for each of the membrane types constructed.

EXAMPLE TWO

Figure 5:
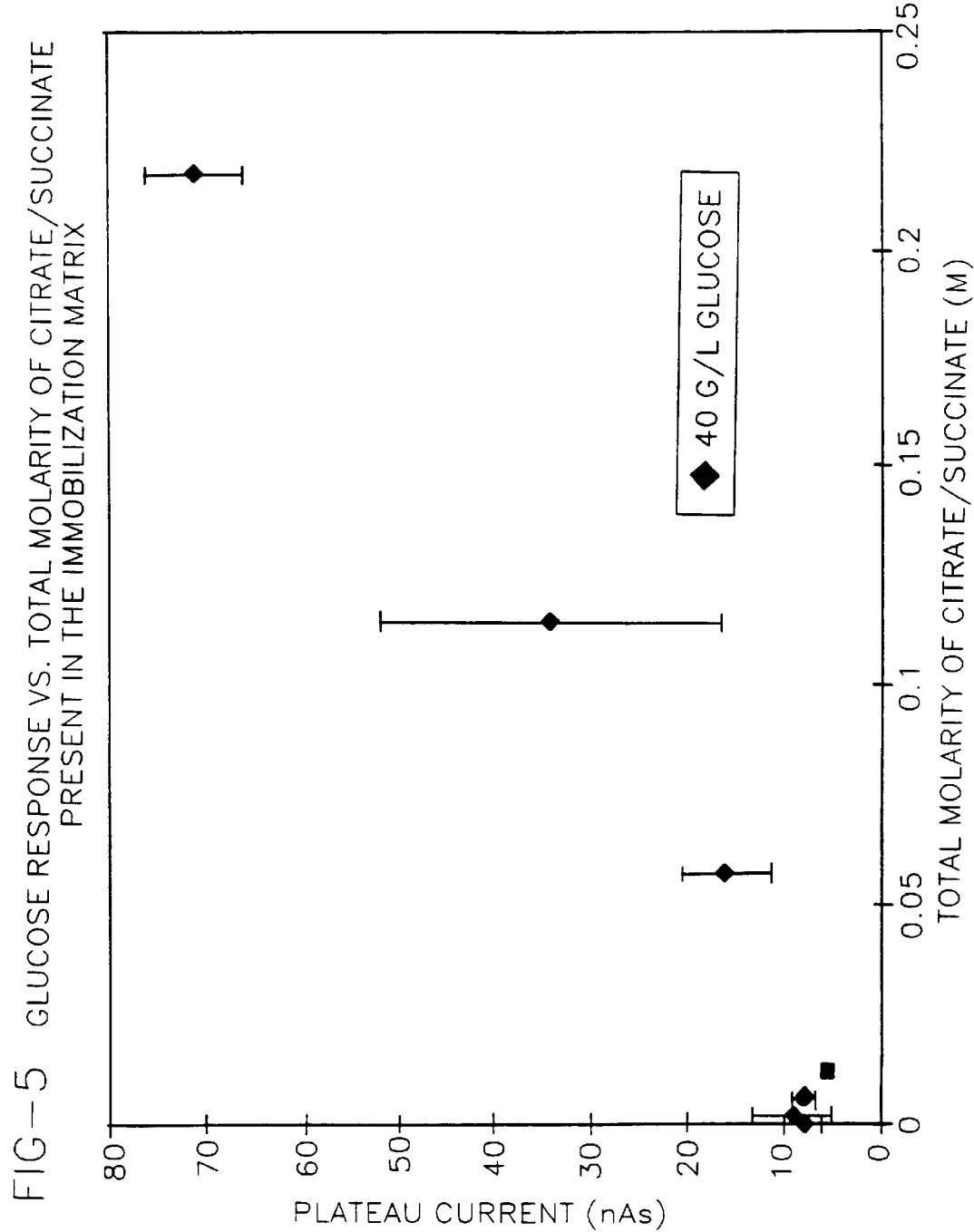
FIG. 5 is a graph plotting plateau current and buffer solution molarity similar to FIG. 2 but showing data obtained with a second laminated membrane construction.
Figure 6:
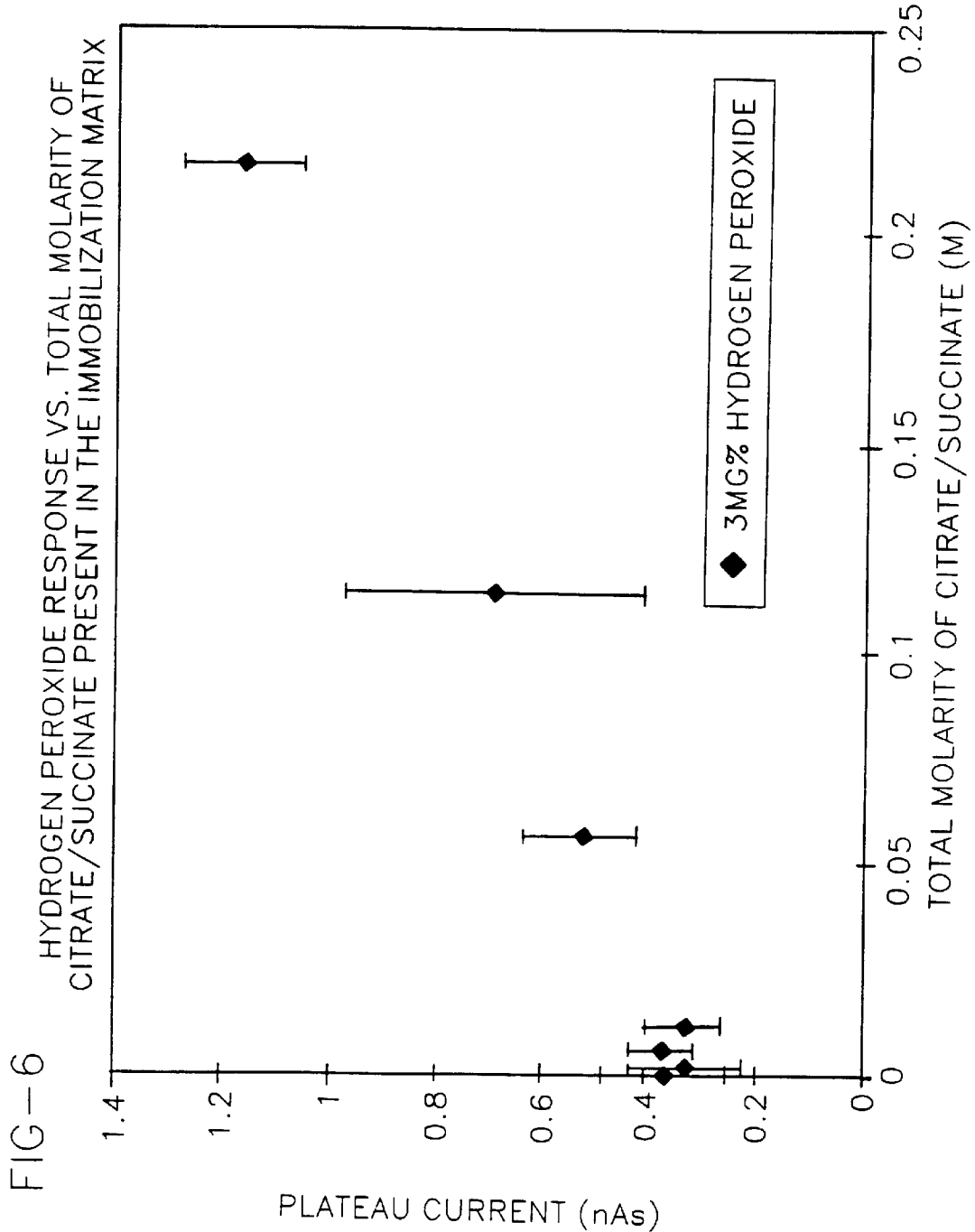
FIG. 6 is a graph plotting plateau current and buffer solution molarity similar to FIG. 3 but showing data obtained with the second laminated membrane construction.
Figure 7:
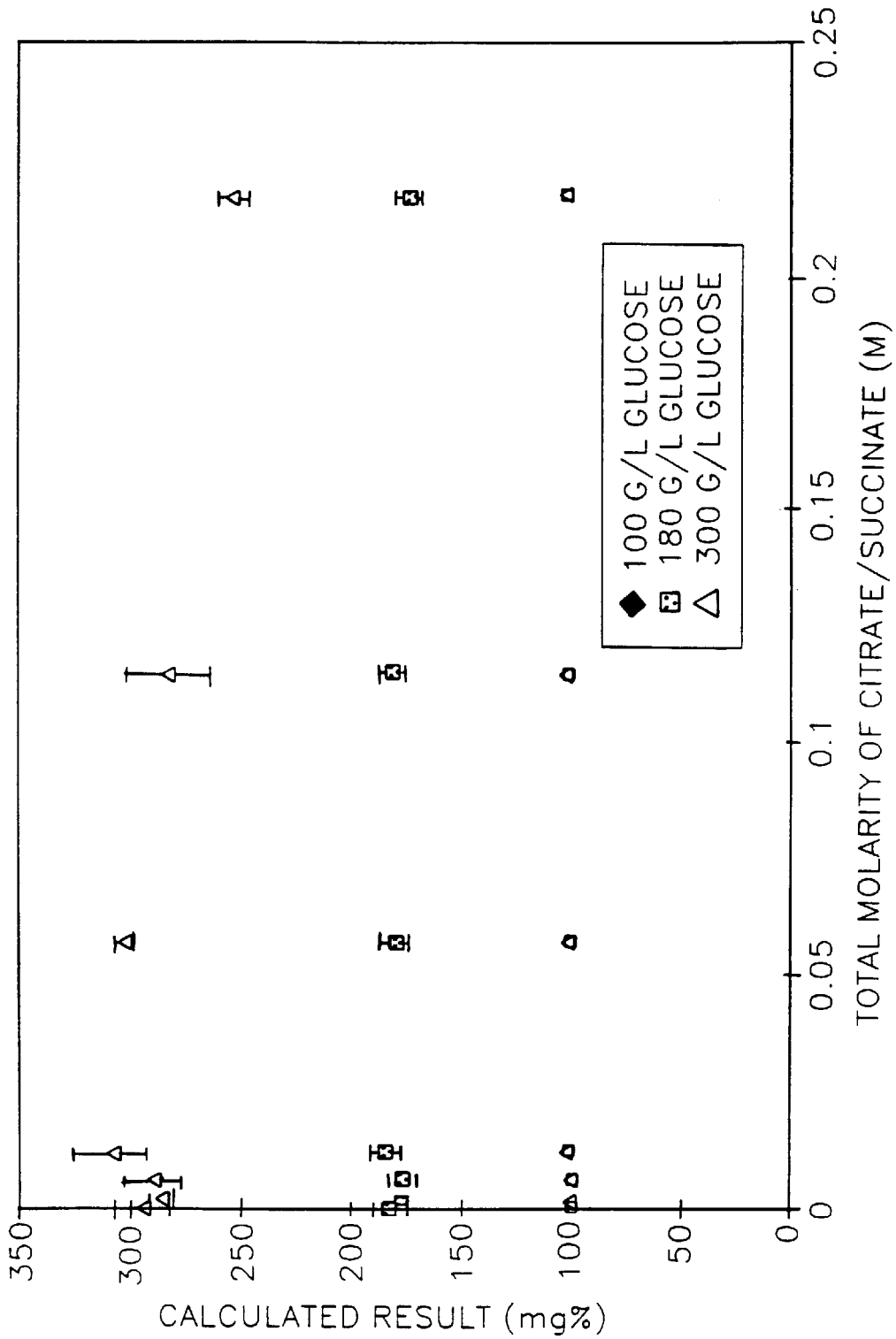
FIG. 7 is a graph plotting glucose concentrations versus buffer solution molarity similar to FIG. 4 but showing data obtained with the second laminated membrane construction.

The procedures reported above for Example One were repeated except that a different support layer construction for the laminated membrane was used. In this example, the support layer 30 was composed of a polycarbonate layer having an average pore size of 686 angstrom units and a pore density of $6 \times 10^6$ pores/cm$^2$. FIGS. 5, 6, and 7 respectively indicate glucose response, hydrogen peroxide response, and calculated glucose measurement.

Figure 2:
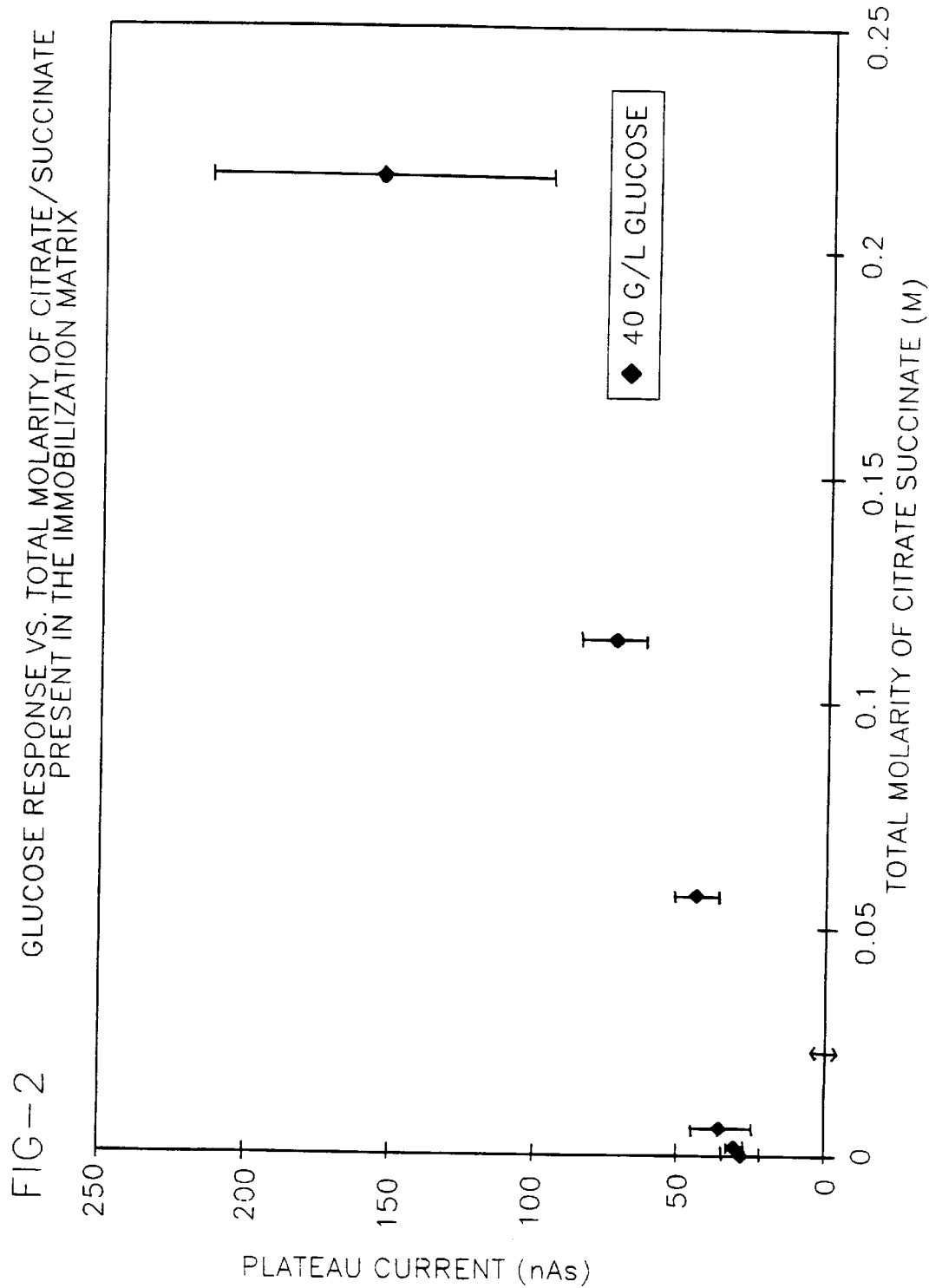
FIG. 2 is a graph plotting plateau current obtained on a YSI Model 2700 polarographic—analytical instrument versus molarity of the buffer solution present during the immobilization of the enzyme located in the enzyme layer of a first laminated membrane construction, used in conjunction with the testing of a 40 g/l glucose sample.
Figure 3:
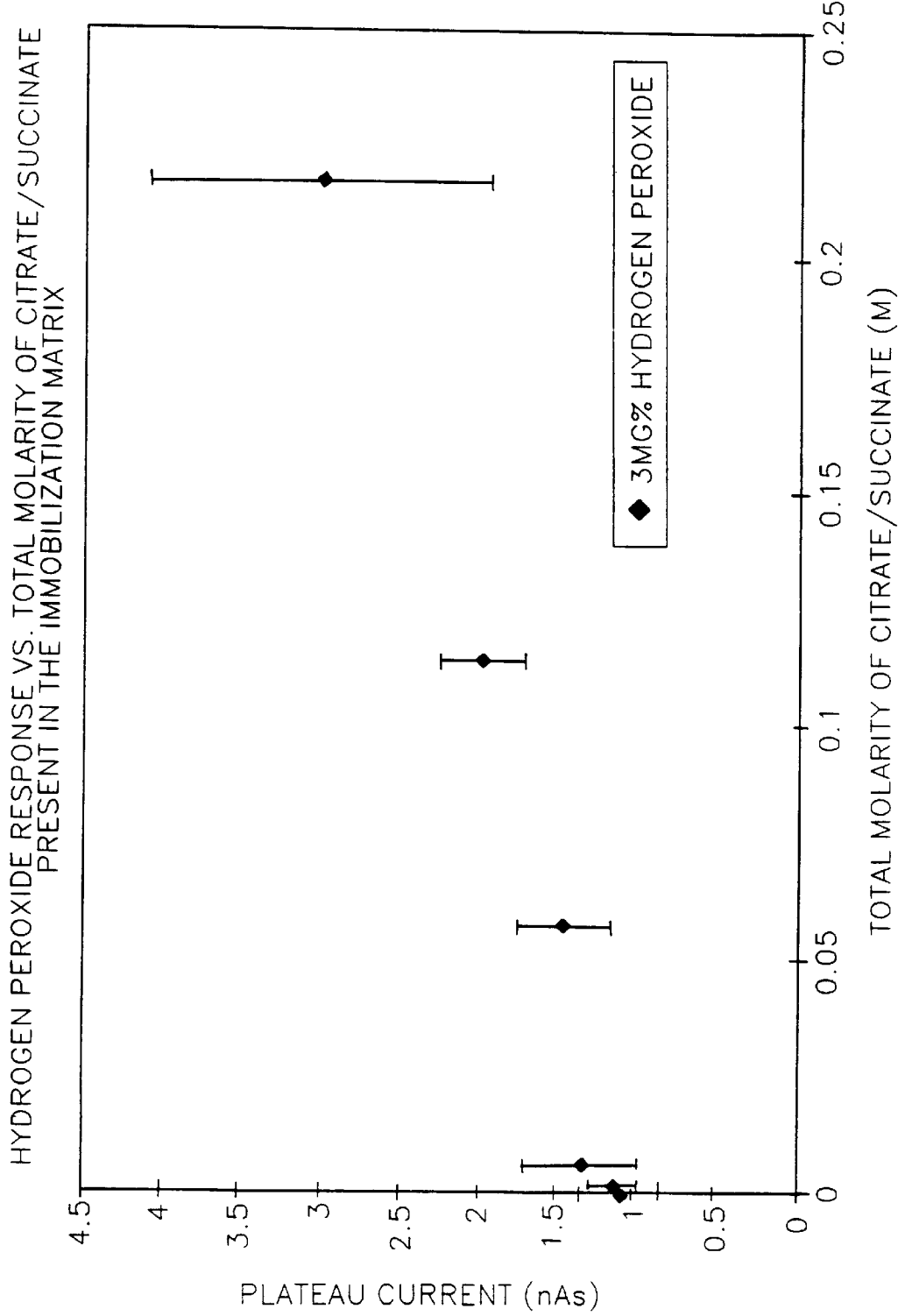
FIG. 3 is a graph plotting plateau current obtained on the YSI Model 2700 versus molarity of the buffer solution used in the preparation of the enzyme layer of the first laminated membrane construction used in conjunction with the testing of a 3 mg % solution of $H_2O_2$.
Figure 4:
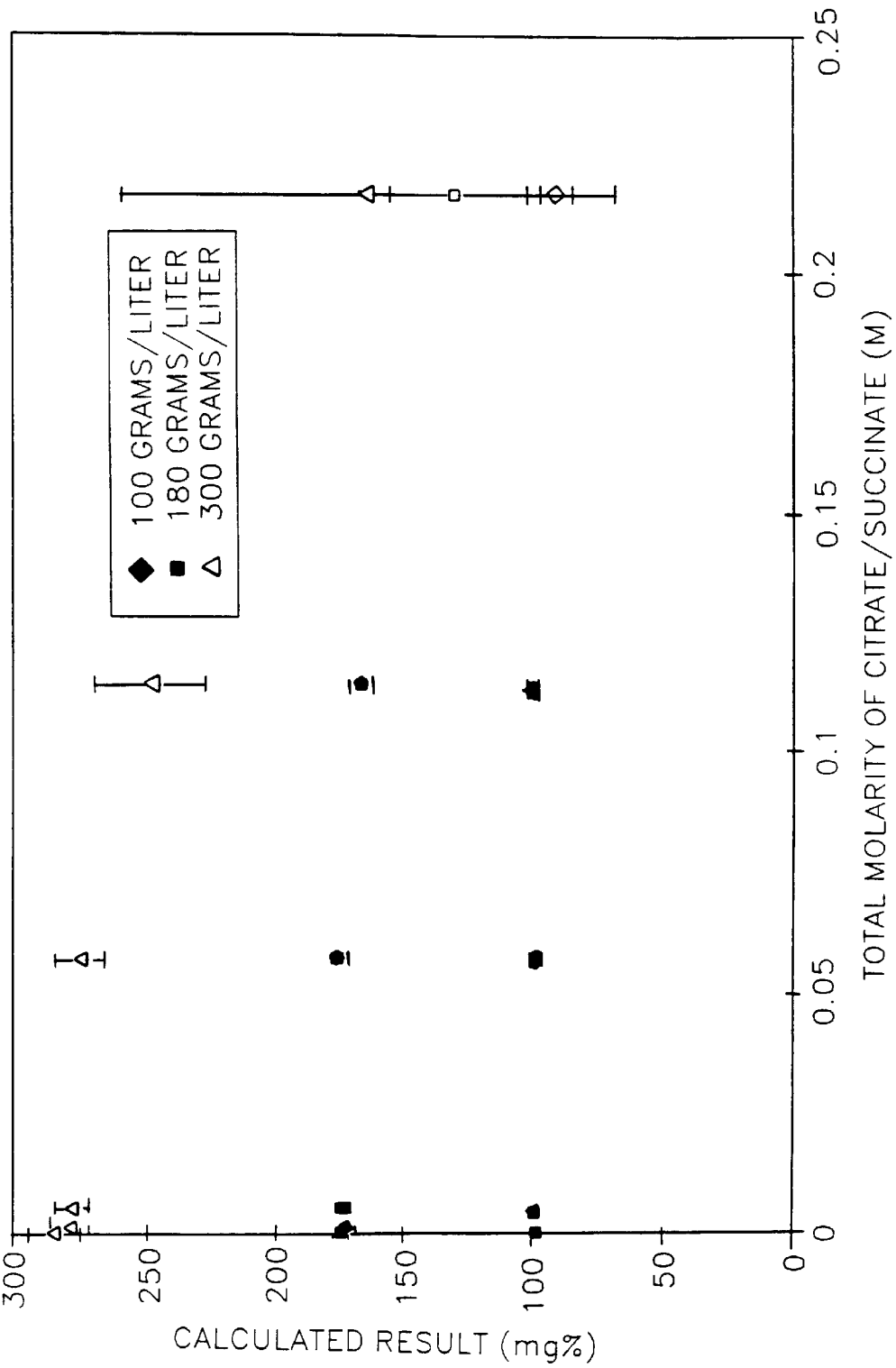
FIG. 4 is a graph plotting glucose concentrations measured on the YSI Model 2700 versus molarity of the buffer solution used in the preparation of the enzyme layer of the first laminated membrane construction.

The results are comparable to those shown in conjunction with FIGS. 2, 3 and 4 and support the conclusion that the buffer salt effect is present at larger pore sizes and lower pore densities.

EXAMPLE THREE

The procedures reported above for Example 1 were repeated except that a different buffer solution and a different support layer 30 structure were used as follows:

buffer solution

NaH$_2$PO$_4$ ) Present in a weight
) ratio of monobasic
Na$_2$H PO$_4$ ) phosphate : dibasic
phosphate approx. = .54:1
pH approx. 7.0 structure of support layer 30 polycarbonate
343 angstrom unit pore diameter
pore density $1 \times 10^8$

Figure 8:
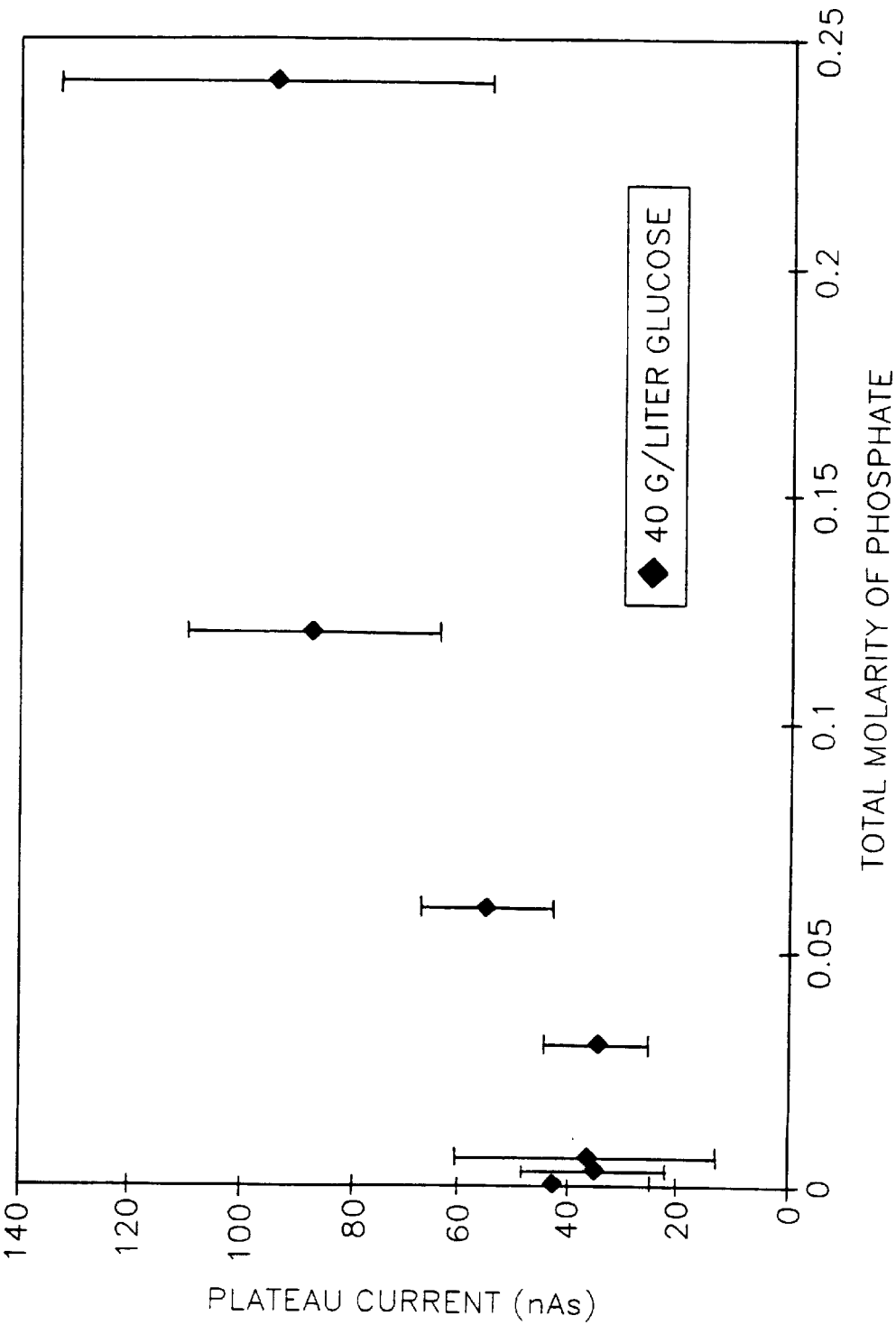
FIG. 8 is a graph similar to FIG. 5 but showing data obtained using a second buffer solution and a third laminated membrane construction.

Data obtained as a result of the Example Three procedures are shown in FIGS. 8–10. These data are totally consistent with that reported for Examples One and Two and again indicate that regardless of buffer type employed and pH, the linear range of the membranes increases as the buffer concentration of the buffer solution used during the enzyme immobilization stage decreases.

It is to be noted that the molarity of the buffer solutions reported above has been referred to with respect to the concentration of buffer in solution as it is admixed with enzyme during the enzyme immobilization phase prior to membrane drying. After drying however, the concentration of buffer remaining in the enzyme layer will generally be about $1 \times 10^{-14}$ to $1 \times 10^{-8}$ moles/cm$^2$ of the enzyme layer.

Although applicant is not to be bound to any particular theory of operation, it appears that the combination of improved dynamic range and decreased sensitivity, which is observed as buffer salt concentration decreases, could only be due to an increase in the density of the enzyme layer. Indeed, there is literature which teaches that the permeability of the immobilized enzyme layer can be important in determining the response characteristics of an enzyme electrode (Neikov, A and Sokolov, S, Analytica Chimica ACTA, 307 (1995) 27–36 and Mutlu, M. and Mutlu, S., Biotechnology Techniques, 9 No. 4 (1995) 277–282). However, no one has ever demonstrated that the density of the enzyme layer in a three-layer Newman style laminate, could be increased to the point that the dynamic range needed for clinical glucose measurement on undiluted whole blood could be obtained.

It should be emphasized that the results depicted in FIGS. 2 through 10 were obtained under circumstances in which the aqueous glucose sample was diluted 1:20 into a preoxygenated and buffered diluent. The glucose concentrations depicted in FIGS. 2, 4, 5, 7, 8 and 10 should therefore be divided by 20 in order to be representative of the actual glucose concentrations seen by the sensor. Thus, if the upper end of the clinically relevant glucose concentration range is 900 mg % or 9 Grams/Liter (undiluted) this concentration would be represented in FIGS. 4, 7 and 10 by the 180 Grams/Liter (20×9 Grams/Liter) data point. Although the data suggests that accuracy at 180 Gram/Liter is not greatly affected by constructing membranes using buffer salt concentrations at or below 0.1 Molar, these results were obtained at higher oxygen concentrations than typically found in whole blood. Since it has been shown that the linearity of sensors of this type are, in general, limited by the oxygen concentration it is presumed that the non-linearity observed for any given membrane type would be worse at lower oxygen concentrations.

EXAMPLE FOUR

In order to prove that the increased dynamic range observed is a result of an increase in the density of the enzyme layer a special glucose oxidase enzyme membrane was constructed whose overall porosity was more dependent on the porosity of the enzyme layer than in the standard three-layer Newman laminate (see above, Example One). This was done by replacing both the outside polycarbonate membrane ($1\times10^8$ pores/cm$^2$, 310 angstroms in diameter) and the inside cellulose acetate layer with a very porous polycarbonate membrane ($6\times10^8$ pores/cm$^2$, 500 angstroms in diameter). Membranes of this construction have been used in other studies of enzyme layer density (Mutlu, M and Mutlu, S, Biotechnology Techniques, 9 No. 4 (1995) 277–282).

All other construction materials (including "salt free" glucose oxidase, BMC catalog #105 147) and processes used were exactly the same as those for the standard laminated membrane. This construction allows the permeability of the enzyme layer to be probed using a larger electroactive molecule than could otherwise be used if the cellulose acetate layer were present. This is important because one would expect that the rate of transport of a larger molecule through the enzyme layer would be more sensitive to changes in the density of the layer than that of a smaller molecule. Ferrocyanide (M.W. =211.9) has been used as such a probe in other similar studies of enzyme layer permeability/density and was used in this work (Castner, J. F. and Wingard, L. B. Biochemistry 23 (1984) 2203–2310; Wingard, L. B., Canton, L. A. and Castner, J. F., Biochemica et Biophysica Acta, Vol. 748, 1983 pp 21–27).

Within thirty-six hours after construction, the special double polycarbonate (DPC) membranes were installed and evaluated on exactly the same set of YSI model 2700 $H_2O_2$ probes as previously used to evaluate the standard membranes. After break-in, responses to both ferrocyanide and $H_2O_2$ were measured at 30 seconds after injection. The 2700 system provides for aperometric measurement of an electrically active species, such as ferrocyanide, at a platinum anode polarized at 0.7V. The electrolyte used in these systems is a 0.05M $PO_4$ buffer with 1.5 g/l NaCl, pH of the electrolyte is 7.2 (i.e., YSI 2357 Buffer).

FIG. 11 depicts the results obtained in this study. The response to both Ferrocyanide and $H_2O_2$ are plotted against the buffer concentration used in the enzyme layer of the DPC membrane. Also plotted is the molar response ratio for ferrocyanide which is calculated by dividing the response to ferrocyanide by the response to an equimolar concentration of $H_2O_2$. This ratio is quite indicative of the actual differences in enzyme layer permeability across the various membrane types because it is normalized in order to eliminate probe to probe and other membrane to membrane differences. This is a result of the fact that the electrode response to $H_2O_2$ is dependent upon all the same factors as is the response to ferrocyanide including the permeability of the polycarbonate layers and working electrode size. However, the differential effect of these factors, except for enzyme layer permeability, is relatively insensitive to the difference in molecular size between $H_2O_2$ and ferrocyanide. This ratio can be used as a quantitative measure of enzyme layer permeability since it is the rate of ferrocyanide transport or flux through the enzyme layer relative to the transport or flux of $H_2O_2$.

It can clearly be seen that the shape of the molar response ratio (Ferrocyanide/$H_2O_2$) vs. buffer salt concentration curve obtained on the DPC membranes (FIG. 11) follows exactly the same trend as does the glucose response vs. buffer salt concentration curve obtained on the standard Newman-type three layer membrane (FIG. 2).

The conclusion is that the improvement in dynamic range (i.e. linearity) observed on standard Newman laminated enzyme membranes which are constructed with decreasing amounts of buffer present in the immobilization matrix is, indeed, due to increased enzyme layer density, ie. decreased permeability.

Furthermore, membranes containing enzyme layers which have a higher density, represented by an average Ferrocyanide/$H_2O_2$ Molar response ratio of 0.05 or less, have an improved linear range compared to membranes with lower densities or average Molar response ratios greater than 0.05 (see FIGS. 4, 7, 10 and 11).

In general, adding anything to the enzyme/immobilizer matrix beyond just enzyme and cross linking agent tends to make the cured enzyme layer less dense and the enzyme electrode less linear. Not only does the dynamic range improve as buffer is removed from the immobilization matrix but the membrane to membrane repeatability also tends to improve (compare the size of error bars at low buffer vs. high buffer in FIGS. 2 through 10). The results with buffer salts indicate that there is a deleterious effect associated with their inclusion in the immobilization matrix. This is against the conventional wisdom which is that buffers need to be included in the matrix in order to control the pH and ionic strength at which the reaction is run (Yacynych, (1992) Advances in Biosensors, Vol. 2 (A. P. F. Turner ed.) pp 24–25 JAI Press Ltd., London, and Chibata, I. (1978) Immobilized Enzymes; Research and Development, p. 9, John Wiley and Sons, New York).

EXAMPLE FIVE

Similar results are obtained when bovine serum albumin (BSA) is incorporated into the immobilization matrix. Membranes were constructed as described in Example One except that various amounts of bovine serum albumin (Fraction V; Sigma catalog # A-4503) were added to the glucose oxidase water mixture used in membrane construction. An equivalent amount of glucose oxidase was left out such that total protein concentration was held constant at 10 mg in 250 uL. Membranes were evaluated in model 2700s as before.

FIG. 12 illustrates how the linearity of sensors, incorporating glucose oxidase layers with increasing concentrations of BSA, decreases while sensitivity increases. The glucose concentrations shown are corrected for dilution and therefore indicate either the actual glucose concentration (abscissa) or the calculated glucose concentration (ordinate) seen by the sensor. The values appearing to the right of each standard curve are the average glucose sensitivities in nAs measured at 2 gram/liter glucose. This is also against the conventional wisdom which suggests that "co-immobilizing" glucose oxidase with BSA is desirable because the BSA somehow stabilizes the enzyme during immobilization (P. Pantano and W. G. Kuhr, Electroanalysis, 7 (1995) 406–416). Although the glucose sensitivity increased with increasing BSA concentrations (even though the glucose oxidase is effectively being diluted!) this was at the expense of a decreased linear range. This, again, is suggestive that the density of the enzyme layer is decreasing as the BSA concentration is increased. It is interesting to note that, to the best of my knowledge, all previous studies of enzyme layer density have involved glucose oxidase that had been co-immobilized with BSA and the possible effects of BSA on layer density were neither recognized nor studied (see Mutlu et al., Castner et al. and Wingard et al. referenced above).

Finally, the phenomena which I have described are not specific to glucose oxidase but also apply to other enzymes. Early results with lactate oxidase support this conclusion.

It is apparent that a variety of modifications can be made by the skilled artisan in carrying out the invention described about in accordance with the description given above. The following claims are intended to cover all such equivalent modifications.

I claim:

1. Laminated membrane for use in a polarographic cell assembly for assay of an analyte in a mixture or solution, said laminated membrane comprising:

an outer layer having pores therein, an inner layer, and an enzyme layer disposed between said outer layer and said inner layer, said enzyme layer comprising a buffer solution therein adapted to maintain a pH of between about 4 to 9.0 in said enzyme layer; said buffer being present in said solution in an amount of between about 0.001 to about 0.050 M.

2. Laminated membrane as recited in claim 1 wherein said buffer is present in said buffer solution in an amount of about 0.001 to 0.005 M.

3. Laminated membrane as recited in claim 1 wherein said enzyme layer is further characterized by exhibiting a molar response ratio of ferrocyanide:$H_2O_2$ of about 0.05 or less.

4. Method of making a laminated membrane assembly for use in the polarographic measurement of an analyte existing in an undiluted blood sample, comprising:

(a) providing a porous outer support layer;

(b) providing an inner barrier layer;

(c) providing an enzyme containing mixture comprising a buffer solution, said buffer solution adapted to maintain a pH of between about 4 to 9.0 in said enzyme containing mixture, said buffer being present in said buffer solution in an amount of about 0.001 to about 0.050 M.

5. Method as recited in claim 4 wherein said buffer is present in said solution in an amount of about 0.001 to about 0.005 M.

6. Method as recited in claim 4 wherein said enzyme containing mixture, after drying, exhibits a molar response ratio of ferrocyanide:$H_2O_2$ of about 0.05 or less.

7. Laminated membrane for use in a polarographic cell assembly for assay of an analyte existing in a sample of undiluted whole blood, plasma or serum, said laminated membrane comprising:

an outer layer having pores therein, an inner layer, and an enzyme layer disposed between said outer layer and said inner layer, said enzyme layer characterized by exhibiting a molar response ratio of ferrocyanide:$H_2O_2$ of about 0.05 or less.

8. Laminated membrane as recited in claim 7 wherein said enzyme layer comprises a buffer solution therein adapted to maintain a pH of between about 4 to 9.0 in said enzyme layer, said buffer being present in said solution in an amount of between about $1 \times 10^{-6}$ to about 0.1 molar.

9. Laminated membrane as recited in claim 7 wherein said buffer is present in said buffer solution in an amount of between about 0.001 to about 0.05 M.

10. Laminated membrane as recited in claim 9 wherein said buffer is present in said buffer solution in an amount of between about 0.001 to about 0.005 M.

11. Laminated membrane for use in a polarographic cell assembly for assay of an analyte in a mixture or solution, said laminated membrane comprising:

an outer layer having pores, an inner layer, and a highly dense enzyme layer disposed between said outer layer and said inner layer, said enzyme layer characterized by exhibiting a molar response ratio of ferrocyanide:$H_2O_2$ of about 0.05 or less.

12. Method of making a laminated membrane assembly for use in the polarographic measurement of an analyte existing in a blood sample, comprising:

(a) providing a porous outer support layer;

(b) providing an inner barrier layer;

(c) providing a high density enzyme containing layer between said outer layer and said inner barrier layer; said high density enzyme layer exhibiting a molar response ratio of ferrocyanide:$H_2O_2$ of about 0.05 or less.

* * * * *